United States Patent
Bae et al.

(10) Patent No.: US 10,604,602 B2
(45) Date of Patent: Mar. 31, 2020

(54) NEODYMIUM COMPOUND AND CATALYST FOR DIENE POLYMERIZATION INCLUDING THE SAME

(71) Applicant: LG CHEM, LTD., Seoul (KR)

(72) Inventors: Hyo Jin Bae, Daejeon (KR); Kyoung Hwan Oh, Daejeon (KR); Sae Young Yun, Daejeon (KR); Jeong Heon Ahn, Daejeon (KR); Woo Jin Cho, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/684,472

(22) Filed: Aug. 23, 2017

(65) Prior Publication Data

US 2018/0037684 A1 Feb. 8, 2018

Related U.S. Application Data

(60) Division of application No. 14/462,172, filed on Aug. 18, 2014, which is a continuation of application No. PCT/KR2014/003686, filed on Apr. 25, 2014.

(30) Foreign Application Priority Data

Sep. 26, 2013 (KR) ........................ 10-2013-0114716
Apr. 22, 2014 (KR) ........................ 10-2014-0048119

(51) Int. Cl.
*C08F 136/06* (2006.01)
*C07F 5/00* (2006.01)

(52) U.S. Cl.
CPC ............ *C08F 136/06* (2013.01); *C07F 5/003* (2013.01)

(58) Field of Classification Search
None
See application file for complete search history.

(56) References Cited

U.S. PATENT DOCUMENTS

| | | |
|---|---|---|
| 4,575,538 A | 3/1986 | Hsieh et al. |
| 5,220,045 A | 6/1993 | Thomas et al. |
| 6,054,563 A | 4/2000 | Alas et al. |
| 6,090,926 A | 7/2000 | Keyer et al. |
| 6,111,082 A | 8/2000 | Yunlu et al. |
| 6,482,906 B1 | 11/2002 | Tocchetto Pires et al. |
| 6,482,930 B1 | 11/2002 | Kwag et al. |

FOREIGN PATENT DOCUMENTS

| | | |
|---|---|---|
| EP | 1055659 A1 | 11/2000 |
| JP | 05-186387 A | 7/1993 |
| JP | 08-109299 A | 4/1996 |
| JP | 2000-63386 A | 2/2000 |
| JP | 2001-511819 A | 8/2001 |
| JP | 2001-261683 A | 9/2001 |
| JP | 2002-512249 A | 4/2002 |
| JP | 2002-517400 A | 6/2002 |
| JP | 2002241420 A | 8/2002 |
| KR | 10-2015-0032017 A | 3/2015 |

OTHER PUBLICATIONS

Kwag (Macromolecules, 2002, 35, 4875-4879 (Year: 2002).*
Evans, William J., et al.: "Lanthanide Carboxylate Precursors for Diene Polymerization Catalysis: Syntheses, Structures, and Reactivity with Et2AlCl", Organometallics, vol. 20, Nov. 29, 2001, pp. 5751-5758.
Zoan, Tu A., et al.: "Synthesis, structure and properties of volatile lanthanide privalates", Journal of Alloys and Compounds, vol. 225, 1995, pp. 396-399.
Gwanghoon Kwag et al., 'A Highly Reactive and Monomeric Neodymium Catalyst', Macromolecules, 2002, 35 (13), pp. 4875-4879.
Andreas Fischbach et al., 'Structure-Reactivity Relationships in Rare-Earth Metal Carboxylate-Based Binary Ziegler-Type Catalysts', Organometallics, vol. 25, No. 7, pp. 1626-1642, 2006.
Zhichao Zhang et al., 'Polymerization of 1,3-Conjugated Dienes with Rare-Earth Metal Precursors', Struct Bond, (2010) 137: 49-108.
Lido Porri et al., "Recent Developments in Lanthanide Catalysts for the CIS-1,4 Polymerization of 1,3-Dienes", Polymer Preprint, 1998, Spring p. 214-215.
U.S. Appl. No. 14/462,172, filed Aug. 18, 2014.

* cited by examiner

*Primary Examiner* — Yun Qian
(74) *Attorney, Agent, or Firm* — Dentons US LLP

(57) ABSTRACT

The present invention relates to a neodymium compound represented by Formula 1 and a catalyst for diene polymerization including the same.

1 Claim, 1 Drawing Sheet

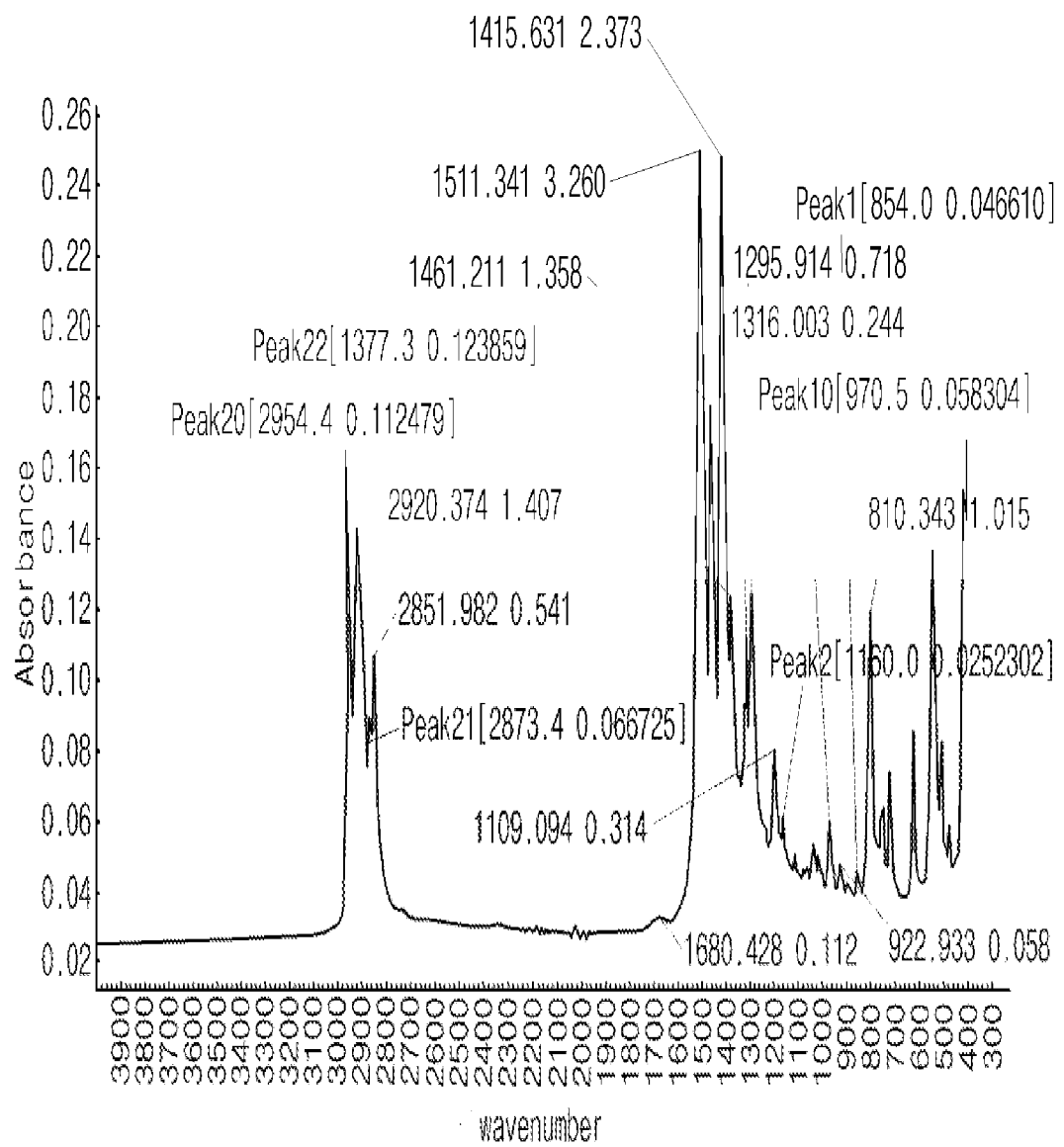

NEODYMIUM COMPOUND AND CATALYST FOR DIENE POLYMERIZATION INCLUDING THE SAME

This is a Divisional of application Ser. No. 14/462,172, filed on Aug. 18, 2014, which is a Continuation Bypass Application of International Application No. PCT/KR2014/003686, filed on Apr. 25, 2014, and claims the benefit of Korean Application No. 10-2014-0048119, filed on Apr. 22, 2014, and Korean Application No. 10-2013-0114716, filed on Sep. 26, 2013, all of which are hereby incorporated by reference in their entirety for all purposes as if fully set forth herein.

TECHNICAL FIELD

The present invention relates to a neodymium compound including a carboxylate ligand containing substituents having various lengths and having a novel structure, and a catalyst for diene polymerization having improved catalytic activity by using the same.

BACKGROUND ART

As demands on a rubber mixture increase in various manufacturing fields such as a tire, impact resistant polystyrene, the sole of a shoe, a golf ball, etc., the value of a butadiene rubber which is an intermediate of petrochemicals increases as an alternative material of a natural rubber of which production is insufficient.

However, as the costs of the main material of the butadiene rubber increases depending on high oil prices, the burden on increasing the prime cost of a synthetic rubber is added.

To decrease the prime cost of the butadiene rubber, development on processing technique of the butadiene rubber is necessary along with the building of additional factories for producing the butadiene rubber.

The butadiene rubber is known to be manufactured by a polymerization system using a catalyst containing a rare earth metal. Particularly, a neodymium compound (Nd(OOCR)$_3$, R=alkyl group) is verified to be particularly effective among the catalysts including the rare earth metal (See Patent Document 1).

However, the catalytic activity of the neodymium compound is at most 7% (See Non-patent Document 1). This result may be obtained due to the following. A common neodymium carboxylate compound is prepared in an aqueous solution and then is extracted using an organic solvent, and neodecanoate is included therein as a ligand. Thus, a large amount of the neodymium carboxylate compound having an oligomer type is present in the product thus obtained. That is, due to the structure of the oligomer type, the production yield of a catalyst active species may be deteriorated, and the catalytic activity may be decreased when used as a catalyst for diene polymerization.

PRIOR ART DOCUMENT

Patent Document

European Patent Publication No. 1 055 659

Non-Patent Document

Polymer Preprint, 1998, Spring p 214

DISCLOSURE OF THE INVENTION

Technical Problem

In order to solve the foregoing limitations, a neodymium compound having a novel structure capable of restraining oligomerization by inducing steric change around a neodymium central metal by introducing a carboxylate ligand containing alkyl groups having various lengths as substituents is provided in the present invention.

In addition, a catalyst for diene polymerization including the neodymium compound, a halogen compound, and an organometal compound, and having improved solubility with respect to a polymerization solvent and improved catalytic activity is provided in the present invention.

Technical Solution

Particularly, in an embodiment of the present invention, a neodymium compound represented by the following Formula 1 is provided.

[Formula 1]

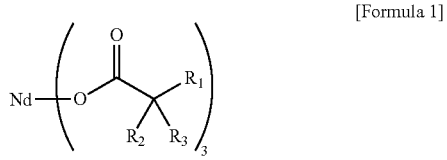

In Formula 1, wherein, $R_1$ is a linear or branched alkyl group having 6 to 12 carbon atoms, $R_2$ and $R_3$ are independently hydrogen, or a linear or branched alkyl group having 2 to 8 carbon atoms, and $R_2$ and $R_3$ are not hydrogen at the same time.

In addition, in an embodiment of the present invention, a catalyst for diene polymerization including the neodymium compound, a halogen compound, and an organometal compound is provided.

Advantageous Effects

As described above, a catalyst for diene polymerization having high efficiency may be provided by providing a neodymium compound introducing a carboxylate ligand containing alkyl groups having various lengths as substituents, and the production efficiency of a diene polymerization process may be improved by using the catalyst.

BRIEF DESCRIPTION OF THE DRAWINGS

The accompanying drawing illustrates a preferred embodiment of the present invention and is included to provide a further understanding of the present invention. The present invention may, however, be embodied in different forms and should not be construed as limited to the accompanying drawing.

FIGURE is a graph illustrating the result of FT-IR analysis with respect to a neodymium compound synthesized in Example 1 according to the present invention.

MODE FOR CARRYING OUT THE INVENTION

Hereinafter, the present invention will be described in more detail to assist the understanding of the present invention.

Here, it will be further understood that terms, such as those defined in commonly used dictionaries, should be interpreted as having a meaning that is consistent with their meaning in the context of the relevant art and will not be interpreted in an idealized or overly formal sense unless expressly so defined herein.

Neodymium Compound

First, as a typical neodymium compound used as a catalyst in a common diene polymerization process is an $Nd(neodecanoate)_3$ compound including a carboxylate ligand having two substituted methyl groups at an α-position. However, in the $Nd(neodecanoate)_3$ compound, a large amount of an oligomer type as in the following Formula 2 is present during polymerizing, and the conversion efficiency into a catalyst active species is deteriorated, and the catalytic activity is low.

[Formula 2]

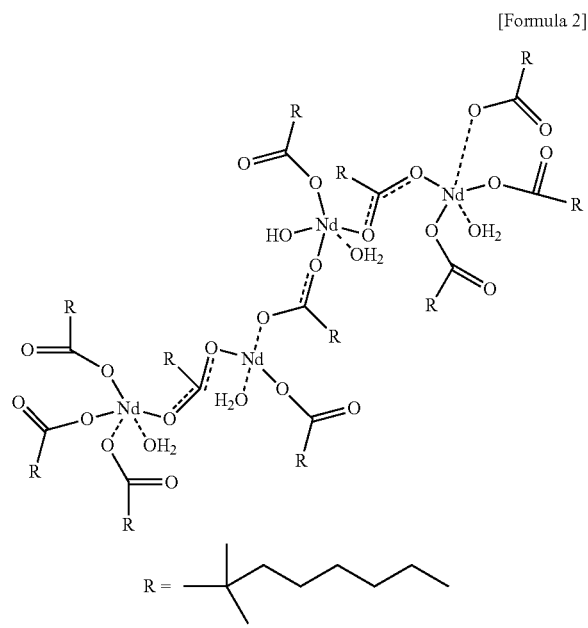

Therefore, to prevent the oligomerization of the neodymium compound in the present invention, a carboxylate including alkyl groups having various lengths as substituents at an α-position is introduced instead of a common neodecanoate group as a ligand of the neodymium compound to restrain the oligomerization due to steric change. Thus, the ratio of neodymium positioned at the central portion and having a difficulty in conversion into the catalyst active species may be decreased to increase the yield of conversion into the catalyst active species, thereby completing the present invention.

Particularly, in an embodiment of the present invention, a neodymium compound represented by the following Formula 1 having high catalytic activity is provided.

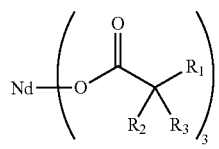

In Formula 1, wherein, $R_1$ is a linear or branched alkyl group having 6 to 12 carbon atoms, $R_2$ and $R_3$ are independently hydrogen, or a linear or branched alkyl group having 2 to 8 carbon atoms, and $R_2$ and $R_3$ are not hydrogen at the same time.

Particularly, in the above Formula 1, $R_1$ is a linear or branched alkyl group having 6 to 8 carbon atoms, $R_2$ and $R_3$ are independently represent hydrogen, or a linear or branched alkyl group having 2 to 6 carbon atoms, and $R_2$ and $R_3$ are not hydrogen at the same time. More particularly, the neodymium compound represented by Formula 1 in the present invention may be selected from the group consisting of $Nd(2,2\text{-diethyl decanoate})_3$, $Nd(2,2\text{-dipropyl decanoate})_3$, $Nd(2,2\text{-dibutyl decanoate})_3$, $Nd(2,2\text{-dihexyl decanoate})_3$, $Nd(2,2\text{-dioctyl decanoate})_3$, $Nd(2\text{-ethyl-2-propyl decanoate})_3$, $Nd(2\text{-ethyl-2-butyl decanoate})_3$, $Nd(2\text{-ethyl-2-hexyl decanoate})_3$, $Nd(2\text{-propyl-2-butyl decanoate})_3$, $Nd(2\text{-propyl-2-hexyl decanoate})_3$, $Nd(2\text{-propyl-2-isopropyl decanoate})_3$, $Nd(2\text{-butyl-2-hexyl decanoate})_3$, $Nd(2\text{-hexyl-2-octyl decanoate})_3$, $Nd(2\text{-t-butyl decanoate})_3$, $Nd(2,2\text{-diethyl octanoate})_3$, $Nd(2,2\text{-dipropyl octanoate})_3$, $Nd(2,2\text{-dibutyl octanoate})_3$, $Nd(2,2\text{-dihexyl octanoate})_3$, $Nd(2\text{-ethyl-2-propyl octanoate})_3$, $Nd(2\text{-ethyl-2-hexyl octanoate})_3$, $Nd(2,2\text{-diethyl nonanoate})_3$, $Nd(2,2\text{-dipropyl nonanoate})_3$, $Nd(2,2\text{-dibutyl nonanoate})_3$, $Nd(2,2\text{-dihexyl nonanoate})_3$, $Nd(2\text{-ethyl-2-propyl nonanoate})_3$, and $Nd(2\text{-ethyl-2-hexyl nonanoate})_3$. Preferably, a compound selected from the group consisting of $Nd(2,2\text{-diethyl decanoate})_3$, $Nd(2,2\text{-dipropyl decanoate})_3$, $Nd(2,2\text{-dibutyl decanoate})_3$, $Nd(2,2\text{-dihexyl decanoate})_3$, and $Nd(2,2\text{-dioctyl decanoate})_3$ may be used.

The weight average molecular weight of the neodymium compound represented by the above Formula 1 may be 800 to 1,400.

In addition, the solubility of the neodymium compound represented by the above Formula 1 means the degree of clear dissolving without turbidity, and is preferably about 4 g of the neodymium compound per 6 g of a nonpolar solvent at room temperature. In addition, the catalytic activity of the neodymium compound represented by the above Formula 1 is preferably greater than or equal to 600 kg[polymer]/mol [Nd]·h in the polymerization time period of 30 minutes.

The neodymium compound as described above includes a carboxylate ligand containing alkyl groups having various lengths as substituents, and steric change is induced around the neodymium central metal to prevent tangling phenomenon between compounds. Thus, the limitation of a common neodymium compound, that is, the oligomerization may be restrained. Since high solubility with respect to a polymerization solvent is secured, the neodymium compound may be used as a catalyst for diene polymerization requiring high activity.

Preparation Method of Neodymium Compound

The neodymium compound of the present invention may be prepared by substituting chlorine of a neodymium (III) chloride hydrate using a ligand substitution reaction. That is, the neodymium compound may be prepared by a ligand-exchange method between neodymium (III) chloride hydrate and a carboxylic acid in the presence of an organic solvent such as ethanol and distilled water. Preferred carboxylic acid may include 2,2-diethyl decanoic acid, 2,2-dipropyl decanoic acid, 2,2-dibutyl decanoic acid, 2,2-dihexyl decanoic acid, 2,2-dioctyl decanoic acid, etc.

Particularly, in an embodiment of the present invention, a method of preparing a neodymium compound including:

preparing a first mixture solution by dissolving an organic acid and an organic base in a mixture solvent of distilled water and an organic solvent;

preparing a second mixture solution by dissolving neodymium chloride hydrate in a mixture solvent of distilled water and an organic solvent;

preparing a third mixture solution by adding drop by drop the first mixture solution in the second mixture solution while stirring;

extracting an organic layer by adding a nonpolar solvent and distilled water after distilling off the organic solvent by distilling the third mixture solution under a reduced pressure; and drying the organic layer, is provided.

In the method of the present invention, the organic solvent is a component for dissolving an organic acid and an organic acid salt, for example, carboxylate and includes, for example, ethanol or tetrahydrofuran.

In addition, the organic acid is not specifically limited only if used as a carboxylate ligand component making a bond with the neodymium central metal and includes, for example, alkyl nonanoic acid or alkyl decanoic acid, which are carboxylic acids. Typically, at least one selected from the group consisting of 2,2-diethyl decanoic acid, 2,2-dipropyl decanoic acid, 2,2-dibutyl decanoic acid, 2,2-dihexyl decanoic acid, and 2,2-dioctyl decanoic acid may be used as the organic acid.

In addition, in the method of the present invention, the organic base is a component for converting an organic acid into an organic acid salt and may include an aqueous sodium hydroxide solution. In this case, the mixing ratio (molar ratio) of the organic acid:organic base may be from 1:0.97 to 1.0. In the case that the amount of the organic base exceeds about 1.0 or is less than about 0.97, a large amount of by-products may be produced, and the yield of the neodymium compound may be decreased.

In addition, in the method of the present invention, the mixing ratio (molar ratio) of the organic acid:neodymium chloride hydrate may be 1.0:0.33 to 0.34. In the case that the amount of the neodymium chloride hydrate is less than 0.33 mol or exceeds 0.34 mol, a large amount of by-products may be produced, and the yield of the neodymium compound may be decreased.

In the method of the present invention, the third mixture solution is preferably obtained by dropping the first mixture solution in the second mixture solution and stirring at room temperature for greater than or equal to 15 hours.

In addition, in the method of the present invention, the nonpolar solvent may use hexane.

In the above-described method of the present invention, the extracting of the organic layer may be repeated by three times or more.

Catalyst for Diene Polymerization

In addition, the neodymium compound prepared by the above-described method is mixed with a halogen compound and an organometal compound in the present invention, and the mixture thus obtained is used as a catalyst for diene polymerization having high solubility with respect to a polymerization solvent.

In this case, each of the compounds used with the neodymium compound will be particularly explained as follows.

First, the kind of the halogen compound is not specifically limited and may include, for example, an aluminum halogen compound, an inorganic halogen compound obtained by substituting aluminum in the aluminum halogen compound with the element selected from the group consisting of boron, silicon, tin or titanium, or an organic halogen compound. The organic halogen compound may be particularly, a t-alkylhalogen compound (an alkyl having 4 to 20 carbon atoms).

In addition, the kind of the organometal compound is not specifically limited and may preferably include, for example, an alkyl aluminum compound, an alkyl magnesium compound, an alkyl lithium compound, etc. Particularly, typical examples of the organometal compound may be trimethyl aluminum, triethyl aluminum, tripropyl aluminum, tributyl aluminum, triisobutyl aluminum, trihexyl aluminum, diisobutyl aluminum hydride, dibutyl magnesium, diethyl magnesium or n-butyl lithium, etc.

In this case, the mixing ratio (molar ratio) of the neodymium compound, the halogen compound and the organometal compound in the catalyst for diene polymerization may be 1.0:1.0 to 20:5.0 to 200, and more preferably, may be 1.0:2.3:12.5.

Diene Polymerization Reaction

In addition, the catalyst for diene polymerization including the neodymium compound, the halogen compound and the organometal compound in the presence of a nonpolar solvent may be added in a solution obtained by mixing diene and a nonpolar solvent, and a polymerization reaction may be conducted at 20 to 200° C. for 15 minutes to 3 hours in the present invention.

In addition, the concentration of the diene compound/nonpolar solvent before adding the catalyst for diene polymerization is preferably 12 to 15 wt % in the polymerization reaction.

In this case, the mixing ratio (molar ratio) of the neodymium compound:diene compound is preferably 1:7,500 to 19,000. The relative mol number of the neodymium compound used is represented with respect to the unit diene amount.

Through polymerizing polydiene using the above-described catalyst system, the catalytic activity may be markedly improved ($1.37 \times 10^3$ kg[polymer]/mol[Nd]·h), and polydiene including greater than or equal to 96% of a 1,4-cis compound may be prepared.

Preferable nonpolar solvents used in the polymerization include nonpolar solvents having no reactivity with the catalyst component, for example, aliphatic hydrocarbon solvents such as pentane, hexane, isopentane, heptane, octane, isooctane, etc.; cycloaliphatic hydrocarbon solvents such as cyclopentane, methylcyclopentane, cyclohexane, methylcyclohexane, ethylcyclohexane, etc.; aromatic hydrocarbon solvents such as benzene, toluene, ethylbenzene, xylene, etc., may be used.

To finish the polymerization reaction of 1,3-butadiene, polyoxyethylene glycol phosphate as a reaction stopper and 2,6-di-t-butyl paracresol as an antioxidant are added. Finally, polybutadiene may be obtained by adding methyl alcohol, ethyl alcohol, or steam and precipitating.

BEST MODE FOR CARRYING OUT THE INVENTION

Hereinafter, the present invention will be explained in more detail referring to example embodiments and comparative example embodiments. The present inventive may, however, be embodied in different forms and should not be construed as limited to the embodiments set forth herein.

EXAMPLES

Preparation of Neodymium Compound

Example 1: Synthesis of Nd(2,2-diethyl decanoate)$_3$

In a 50 ml round-bottomed flask containing 0.82 g (3.6 mmol) of 2,2-diethyl decanoic acid, 10 ml of ethanol was added, following by stirring at room temperature for 10 minutes. In the solution, 3.6 ml (3.6 mmol) of a 1.0 M aqueous sodium hydroxide solution was added and stirred at room temperature for 1 hour to prepare a first mixture solution.

In a 250 ml round-bottomed flask, 0.43 g (1.20 mmol) of neodymium chloride hydrate was added, and 20 ml of hexane and 10 ml of ethanol were added thereto for dissolution to prepare a second mixture solution.

The first mixture solution was put in a dropping funnel and was dropped into the second mixture solution at room temperature to prepare a third mixture solution. After finishing the dropping, the third mixture solution was stirred at room temperature for 15 hours.

The third mixture solution was distilled under a reduced pressure to remove all of the solvents, and 50 ml of hexane and 50 ml of distilled water were added thereto. The solution thus obtained was put in a separating funnel, and an organic layer was extracted three times. The organic layers were collected, and sodium sulfate was added, followed by stirring at room temperature for 10 minutes and filtering. The solution obtained after filtering was distilled under a reduced pressure to remove the solvents. As a result, 0.7 g (yield 80%) of the title compound represented by the following Formula was produced as a white solid that may dissolve in hexane (See FIGURE).

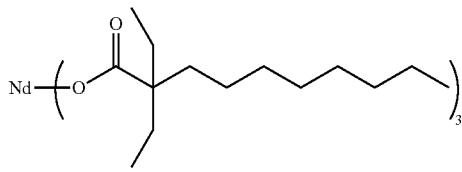

FT-IR: ν2954, 2920, 2873, 2852, 1680, 1511, 1461, 1415, 1377, 1317, 1296, 1199 cm$^{-1}$

Example 2: Synthesis of Nd(2,2-propyl decanoate)$_3$

In a 50 ml round-bottomed flask containing 1.0 g (3.9 mmol) of 2,2-dipropyl decanoic acid, 10 ml of ethanol was added, following by stirring at room temperature for 10 minutes. In the solution, 3.9 ml (3.9 mmol) of a 1.0 M aqueous sodium hydroxide solution was added and stirred at room temperature for 1 hour to prepare a first mixture solution.

In a 250 ml round-bottomed flask, 0.47 g (1.30 mmol) of neodymium chloride hydrate was added, and 20 ml of hexane and 10 ml of ethanol were added thereto for dissolution to prepare a second mixture solution.

The first mixture solution was put in a dropping funnel and was dropped into the second mixture solution at room temperature to prepare a third mixture solution. After finishing the dropping, the third mixture solution was stirred at room temperature for 15 hours.

The third mixture solution was distilled under a reduced pressure to remove all of the solvents, and 50 ml of hexane and 50 ml of distilled water were added thereto. The solution thus obtained was put in a separating funnel, and an organic layer was extracted three times. The organic layers were collected, and sodium sulfate was added, followed by stirring at room temperature for 10 minutes and filtering. The solution obtained after filtering was distilled under a reduced pressure to remove the solvents. As a result, 1.1 g (yield 98%) of the title compound represented by the following Formula was produced as a yellowish blue liquid that may dissolve in hexane.

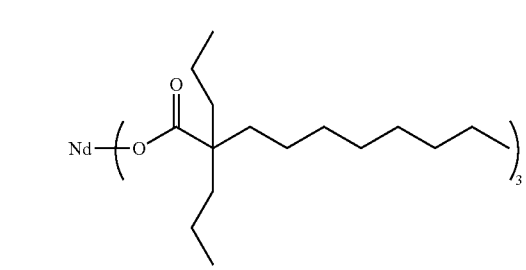

FT-IR: ν2955, 2923, 2853, 1682, 1555, 1503, 1453, 1411, 1360, 1307, 1288, 1261, 1185 cm$^{-1}$

Example 3: Synthesis of Nd(2,2-dibutyl decanoate)$_3$

In a 50 ml round-bottomed flask containing 1.42 g (5.0 mmol) of 2,2-dibutyl decanoic acid, 20 ml of ethanol was added, following by stirring at room temperature for 10 minutes. In the solution, 5.0 ml (5.0 mmol) of a 1.0 M aqueous sodium hydroxide solution was added and stirred at room temperature for 1 hour to prepare a first mixture solution.

In a 250 ml round-bottomed flask, 0.67 g (1.67 mmol) of neodymium chloride hydrate was added, and 30 ml of hexane and 20 ml of ethanol were added thereto for dissolution to prepare a second mixture solution.

The first mixture solution was put in a dropping funnel and was dropped into the second mixture solution at room temperature to prepare a third mixture solution. After finishing the dropping, the third mixture solution was stirred at room temperature for 15 hours.

The third mixture solution was distilled under a reduced pressure to remove all of the solvents, and 50 ml of hexane and 50 ml of distilled water were added thereto. The solution thus obtained was put in a separating funnel, and an organic layer was extracted three times. The organic layers were collected, and sodium sulfate was added, followed by stirring at room temperature for 10 minutes and filtering. The solution obtained after filtering was distilled under a reduced pressure to remove the solvents. As a result, 1.64 g (yield 99%) of the title compound represented by the following Formula was produced as a yellowish blue solid that may dissolve in hexane.

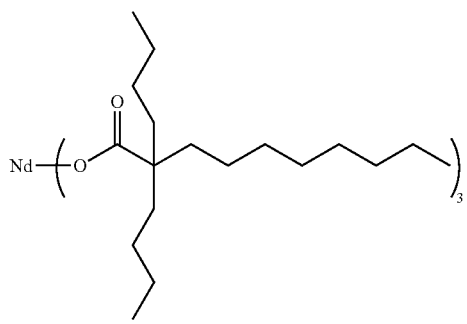

FT-IR: ν2954, 2923, 2855, 1669, 1553, 1504, 1457, 1410, 1306, 1263, 1235 cm$^{-1}$

Example 4: Synthesis of Nd(2,2-dihexyl decanoate)₃

In a 50 ml round-bottomed flask containing 0.35 g (1.0 mmol) of 2,2-dihexyl decanoic acid, 10 ml of ethanol was added, following by stirring at room temperature for 10 minutes. In the solution, 1.0 ml (1.0 mmol) of a 1.0 M aqueous sodium hydroxide solution was added and stirred at room temperature for 1 hour to prepare a first mixture solution.

In a 250 ml round-bottomed flask, 0.125 g (0.35 mmol) of neodymium chloride hydrate was added, and 20 ml of hexane and 10 ml of ethanol were added thereto for dissolution to prepare a second mixture solution.

The first mixture solution was put in a dropping funnel and was dropped into the second mixture solution at room temperature to prepare a third mixture solution. After finishing the dropping, the third mixture solution was stirred at room temperature for 15 hours.

The third mixture solution was distilled under a reduced pressure to remove all of the solvents, and 50 ml of hexane and 50 ml of distilled water were added thereto. The solution thus obtained was put in a separating funnel, and an organic layer was extracted three times. The organic layers were collected, and sodium sulfate was added, followed by stirring at room temperature for 10 minutes and filtering. The solution obtained after filtering was distilled under a reduced pressure to remove the solvents. As a result, 0.38 g (yield 94%) of the title compound represented by the following Formula was produced as a yellowish blue solid that may dissolve in hexane.

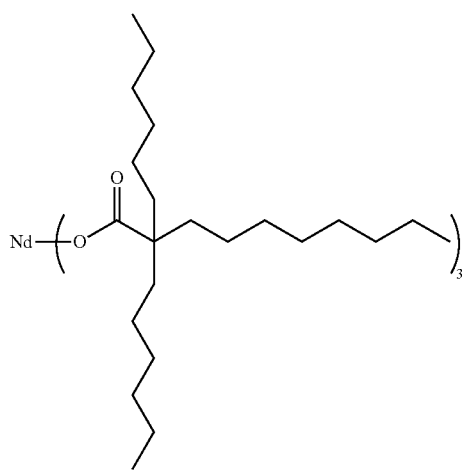

FT-IR: ν2953, 2921, 2852, 1664, 1557, 1505, 1457, 1412, 1377, 1311, 1263 cm⁻¹

Example 5: Synthesis of Nd(2,2-dioctyl decanoate)₃

In a 50 ml round-bottomed flask containing 0.99 g (2.50 mmol) of 2,2-dioctyl decanoic acid, 10 ml of ethanol was added, following by stirring at room temperature for 10 minutes. In the solution, 2.50 ml (2.50 mmol) of a 1.0 M aqueous sodium hydroxide solution was added and stirred at room temperature for 1 hour to prepare a first mixture solution.

In a 250 ml round-bottomed flask, 0.298 g (0.83 mmol) of neodymium chloride hydrate was added, and 20 ml of hexane and 10 ml of ethanol were added thereto for dissolution to prepare a second mixture solution.

The first mixture solution was put in a dropping funnel and was dropped into the second mixture solution at room temperature to prepare a third mixture solution. After finishing the dropping, the third mixture solution was stirred at room temperature for 15 hours.

The third mixture solution was distilled under a reduced pressure to remove all of the solvents, and 50 ml of hexane and 50 ml of distilled water were added thereto. The solution thus obtained was put in a separating funnel, and an organic layer was extracted three times. The organic layers were collected, and sodium sulfate was added, followed by stirring at room temperature for 10 minutes and filtering. The solution obtained after filtering was distilled under a reduced pressure to remove the solvents. As a result, 0.89 g (yield 80%) of the title compound represented by the following Formula was produced as a yellowish blue liquid that may dissolve in hexane.

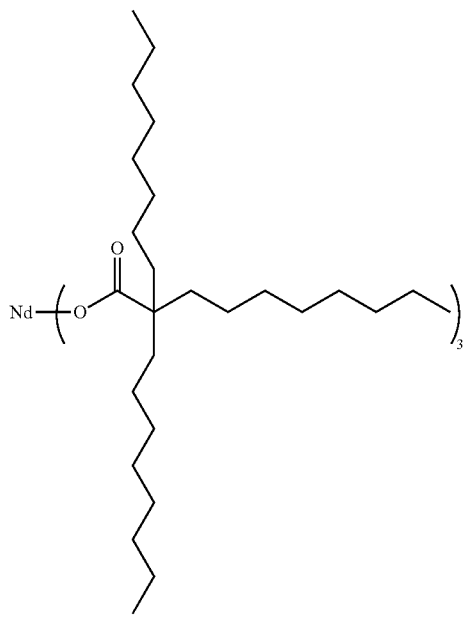

FT-IR: ν2954, 2923, 2855, 1669, 1553, 1504, 1457, 1410, 1306, 1263, 1235 cm⁻¹

Comparative Example 1: Synthesis of Nd(neodecanoate)₃

In a 100 ml round-bottomed flask containing 4.32 g (25 mmol) of neodecanoic acid, 100 ml of ethanol was added, following by stirring at room temperature for 10 minutes. In the solution, 25 ml (25 mmol) of a 1.0 M aqueous sodium hydroxide solution was added and stirred at room temperature for 1 hour to prepare a first mixture solution.

In a 500 ml round-bottomed flask, 3.0 g (8.3 mmol) of neodymium chloride hydrate was added, and 150 ml of hexane and 100 ml of ethanol were added thereto for dissolution to prepare a second mixture solution.

The first mixture solution was put in a dropping funnel and was dropped into the second mixture solution at room temperature to prepare a third mixture solution. After finishing the dropping, the third mixture solution was stirred at room temperature for 15 hours.

The third mixture solution was distilled under a reduced pressure to remove all of the solvents, and 100 ml of hexane and 100 ml of distilled water were added thereto. The solution thus obtained was put in a separating funnel, and an organic layer was extracted three times. The organic layers were collected, and sodium sulfate was added, followed by stirring at room temperature for 10 minutes and filtering. The solution obtained after filtering was distilled under a reduced pressure to remove the solvents. 5.3 g (yield 96%) of the title compound commonly used and represented by the following Formula was produced as a violet solid that may dissolve in hexane.

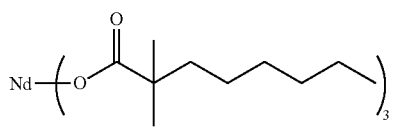

FT-IR: ν2956, 2926, 2872, 1512, 1462, 1411, 1375, 1181, 641 cm$^{-1}$ (Polymerization Example 1) Diene Polymerization Reaction In a completely dried organic reactor, vacuum and nitrogen were alternately applied. Then, in the organic reactor of a vacuum state, 150 g of a mixture solution of 12 wt % (0.3328 mol) of 1,3-butadiene/hexane was added. In the organic reactor, a mixture solution of the neodymium compound (0.044 mmol) of Example 1, diisobutylaluminum hydride (0.55 mmol) and diethyl aluminum chloride (0.10 mmol, 1.0 M in hexane) was added, and a polymerization reaction was conducted at 70° C. for 15 minutes and 30 minutes, respectively. After completing the reaction, a portion of the reactant was taken to measure conversion ratio, and catalytic activity was calculated based thereon. The results are illustrated in the following Table 1.

Polymerization Example 2

A polymerization reaction was conducted according to the same method as the above Polymerization Example 1 except for using the neodymium compound of Example 2 instead of the neodymium compound of Example 1. After completing the reaction, a portion of the reactant was taken to measure conversion ratio, and catalytic activity was calculated based thereon. The results are illustrated in the following Table 1.

Polymerization Example 3

A polymerization reaction was conducted according to the same method as the above Polymerization Example 1 except for using the neodymium compound of Example 3 instead of the neodymium compound of Example 1. After completing the reaction, a portion of the reactant was taken to measure conversion ratio, and catalytic activity was calculated based thereon. The results are illustrated in the following Table 1.

Polymerization Example 4

A polymerization reaction was conducted according to the same method as the above Polymerization Example 1 except for using the neodymium compound of Example 4 instead of the neodymium compound of Example 1. After completing the reaction, a portion of the reactant was taken to measure conversion ratio, and catalytic activity was calculated based thereon. The results are illustrated in the following Table 1.

Comparative Polymerization Example 1

A polymerization reaction was conducted according to the same method as the above Polymerization Example 1 except for using the neodymium compound of Comparative Example 1 instead of the neodymium compound of Example 1. After completing the reaction, a portion of the reactant was taken to measure conversion ratio, and catalytic activity was calculated based thereon. The results are illustrated in the following Table 1.

TABLE 1

| Division | Conversion ratio (%) | | Catalytic activity (kg[polymer]/mol[Nd] · h) | |
|---|---|---|---|---|
| | 15 minutes | 30 minutes | 15 minutes | 30 minutes |
| Example 1 | 82% | 97% | 1367 | 804 |
| Example 2 | 68% | 87% | 1122 | 725 |
| Example 3 | 73% | 90% | 1217 | 750 |
| Example 4 | 65% | 88% | 1084 | 733 |
| Comparative Example 1 | 62% | 73% | 1033 | 608 |

In this case, The conversion ratio was calculated by using the ratio of a value obtained by measuring the weight ratio of a portion of a polymer mixture after completing the polymerization reaction and a value obtained by measuring the weight of polydiene remaining after removing the hexane solvent and residual butadiene by heating a portion of the polymer mixture at 120° C. for 10 minutes. The catalytic activity was calculated by using the weight of the polydiene produced based on the conversion ratio, the mole number of the neodymium compound used in the polymerization reaction and polymerization time period.

As shown in the above Table 1, it may be confirmed that the catalytic activity was relatively higher when using the neodymium compounds of Examples 1 to 4 including carboxylates containing alkyl substituents having various lengths at an α position as ligands as the catalyst for diene polymerization, when compared to that using the neodymium compound of Comparative Example 1 including a common neodecanoate ligand.

The invention claimed is:
1. A catalyst composition for diene polymerization carried out at 70° C. for 15 or 30 minutes, comprising: a neodymium compound selected from the group consisting of: Nd(2,2-diethyl decanoate)$_3$, Nd(2,2-di-n-propyl decanoate)$_3$, Nd(2,2-di-n-butyl decanoate)$_3$, and Nd(2,2-di-n-hexyl decanoate)$_3$;
diethyl aluminum chloride, and diisobutyl aluminum hydride,
wherein a molar ratio of the neodymium compound: diethyl aluminum chloride:diisobutyl aluminum hydride is 0.44:1:5.5.

* * * * *